United States Patent [19]

Sanborn

[11] Patent Number: 4,536,497
[45] Date of Patent: Aug. 20, 1985

[54] S-(1-(1-CYANO-1-(HALOMETHYL)ALKYL-THIO)ALKYL) PHOSPHOROTHIOIC COMPOUNDS AS PESTICIDES

[75] Inventor: James R. Sanborn, Modesto, Calif.

[73] Assignee: Shell Oil Company, Houston, Tex.

[21] Appl. No.: 520,883

[22] Filed: Aug. 5, 1983

[51] Int. Cl.³ .................. A01N 57/12; C07F 9/165
[52] U.S. Cl. ................................. 514/112; 260/940
[58] Field of Search ..................... 260/940; 424/210

[56] References Cited

U.S. PATENT DOCUMENTS 2,908,604 10/1959 Godfrey et al. ................ 424/210
3,706,280 12/1972 Hoffmann et al. .............. 260/940

OTHER PUBLICATIONS

Horning et al., "J.A.C.S.", vol. 69, (1947), pp. 2929-2932.
Davies et al., "Aust. J. of Chem.", vol. 4, (1953), p. 152.

Primary Examiner—Anton H. Sutto

[57] ABSTRACT

Novel compounds of the formula I

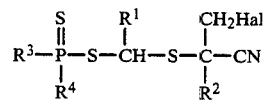

wherein $R^1$ and $R^2$ each is methyl or ethyl, $R^3$ and $R^4$ each is alkyl, alkoxy or mono- or dialkylamino, and Hal is Cl or Br, are useful as pesticides, particularly against soil insects.

9 Claims, No Drawings

S-(1-(1-CYANO-1-(HALOMETHYL)ALKYLTHIO)ALKYL) PHOSPHOROTHIOIC COMPOUNDS AS PESTICIDES

BACKGROUND OF THE INVENTION

1. Field of the Invention

The present invention relates to novel S-(1-(1-cyano-1-(halomethyl)alkylthio)alkyl) phosphorothioic compounds, their use as pesticides and to pesticidal compositions containing these novel compounds.

2. Description of the Prior Art

Some cyano substituted phosphoric, phosphonic and phosphinic esters are known broadly as pesticides. U.S. Pat. No. 3,706,280 discloses cyano-substituted (chloromethylthio)methyl phosphorothioic and phosphonic acid esters useful as miticides and insecticides, particularly against sucking and biting insects and mites.

Applicant has discovered new S-(1-(1-cyano-1-(halomethyl)alkylthio)alkyl) phosphorodithioic compounds having high pesticidal activity, which compounds were not known in the prior art.

SUMMARY OF THE INVENTION

The present invention is directed to novel compounds of the formula I

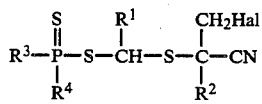

wherein $R^1$ and $R^2$ each independently is a methyl group or an ethyl group and $R^3$ and $R^4$ each independently is an alkyl group, an alkoxy group or a mono- or dialkylamino group, the alkyl portion of each group containing from 1 to 4 carbon atoms and Hal is a chlorine or bromine atom. The compounds are useful as pesticides, particularly against soil insects.

Non-limiting examples of species within the scope of the invention include:

S-(1-(1-cyano-1-(chloromethyl)ethylthio)ethyl) O-ethyl N-isopropylphosphoramidodithioate, S-(1-(1-cyano-1-(chloromethyl)propylthio)ethyl) O,S-diethylphosphorodithioate, S-(1-(1-cyano-1-(bromomethyl)ethylthio)ethyl) O-ethyl N,N-diethylphosphoramidodithioate.

In the compounds of formula I, preferably $R^1$ and $R^2$ each is a methyl group.

In the compounds of formula I, preferably $R^3$ and $R^4$ each independently is an alkoxy group containing 1 to 2 carbon atoms. In one embodiment, $R^3$ and $R^4$ each is an ethyl group.

In another embodiment of these esters of the invention, Hal is preferably a chlorine atom, especially when $R^1$ and $R^2$ are methyl groups.

The S-(1-(1-cyano-1-(halomethyl)alkylthio)alkyl) phosphorodithioates of formula I of the present invention are prepared first by forming intermediate alpha-cyano thioethers of formula II below

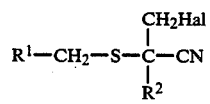

wherein $R^1$ and $R^2$ each is a methyl group or an ethyl group and Hal is a chlorine or bromine atom such that $R^1$, $R^2$ and Hal correspond to those substituents desired in the compounds of formula I of the invention. The alpha-cyano thioether intermediates of formula II are chlorinated at the position alpha to the sulfur atom using conventional chlorinating agents, such as N-chlorosuccinimide, e.g. as taught in Ono, N. et al., *Synthesis*, page 1003 (1981) or sulfuryl chloride, e.g. as taught in Truce, W. E. et al., *J. Amer. Chem. Soc.*, 74, page 3594 (1952). The resulting alpha-cyano alpha-chloro thioethers are then treated with a salt of a dithioic acid (phosphoric, or phosphonic). When $R^3$ and $R^4$ are to be mono- or dialkylamino, the corresponding O-alkyl phosphorodichlorothionate is treated sequentially with a mono- or dialkylamine followed by alkaline hydrogen sulfide.

The alpha-cyano thioether intermediates of formula II are known kinds of compounds and are prepared by conventional techniques (W. A. Thaler et al., *J. Amer. Chem. Soc.*, 90, 2069 (1968). In one representative method, a dialkyl disulfide in which the alkyl groups correspond to $R^1CH_2$ in formula II is treated with sulfuryl chloride or bromide at low temperature followed by treating the resulting sulfenyl halide with an alpha-alkyl-2-propenenitrile or an alpha-alkyl-2-butenenitrile.

The compounds of the invention have exhibited pesticidal, particularly insecticidal, activity. For application, they are generally applied most effectively by formulating them with a suitable inert carrier or surface-active agent, or both. The invention therefore provides a pesticidal composition which comprises as active ingredient a compound of Formula I, together with an inert carrier or surface-active agent, or both. The invention also provides a method of combatting pests at a locus, which comprises applying to that locus a compound of Formula I or a pesticidal composition according to the invention.

The term "carrier" as used herein means an inert or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone, isophorone, and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

The method of applying a compound of this invention to control pests, e.g. insects or mites, comprises applying the compound, ordinarily in a composition of one of the aforementioned types, to a locus or area to be protected from the pests, such as the foilage and/or the fruit of plants. The compound, of course, is applied in an amount sufficient to effect the desired action. This dosage is dependent upon many factors, including the carrier employed, the method and conditions of the application, whether the formulation is present at the locus in the form of an aerosol, or as a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of this invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

In one embodiment of the invention, the compounds of the invention, particularly when $R^1$ is a methyl group, are useful for control of insect pests and their larvae in the soil, which are damaging to plants and the method of such control comprises applying to the soil containing said pests or to their larvae an effective amount of a compound of formula I of the invention.

The compounds of formula I of the invention are useful for controlling a variety of insects in the soil which are damaging to growing plants. The compounds of the invention are well suited for the control of *Diabrotica* species, for example, *Diabrotica virgifera* LeConte, *Diabrotica longicornis* (Say), and *Diabrotica undecimpunctata howardi* Barber, the western, northern and southern corn rootworm, respectively, particularly in their larval stages. Because the compounds of the invention have unusually good larvicidal activity, they may be advantageously used against rootworms, cutworms and wireworms, for example, larvae of *Diabrotica* (rootworms), *Agrotis, Crymodes, Amathes, Euxoa, Peridroma, Lacinipolia, Nephelodes, Actebia, Feltia, Loxagrotis,* (cutworms), *Agriotes, Limonius, Horiatonotus, Ctenicera, Conoderus* (wireworms) and the like. Some of the better known larval species of the above are: *Agrotis ipsilon* (Hufnagel) (black cutworm), *Agriotes mancus* (Say) (wheat wireworm) and particularly the three *Diabrotica* species mentioned above.

For use as soil insecticides, the compounds of the invention are suitably applied to the soil at a rate of from about 0.1 to about 11 kg/ha. Good control of soil inhabiting insects or their larvae is obtained at rates of from about 0.1 to about 5 kg/ha, and especially from about 0.1 to about 4 kg/ha. The compounds of the invention can conveniently be formulated for use as granules or powders containing a solid diluent, impregnated with the compound of the invention. Such formulations usually contain from about 1 to about 50% by weight of the compound of the invention. More effective control results when the formulation is physically lightly mixed with the topsoil. The mixing is preceded or immediately followed by planting seeds which germinate into plants. The compounds of the invention can also be applied as a drench, that is as a solution or dispersion of compounds of the invention in non-phytotoxic solvent or liquid diluent, suitably water. Such drenches can be prepared by diluting with water a concentrate containing the compounds of the invention, an emulsifying agent, and preferably an organic solvent, such as toluene. The compounds of the invention can be applied as a band, furrow or side dress, either incorporated or not.

ILLUSTRATIVE EMBODIMENTS

The invention is illustrated by the following embodiments, which describe the preparation of typical species of the invention. The embodiments are for the purpose of illustration and should not be regarded as limiting the invention in any way. The identity of the products, including intermediates, was confirmed by elemental, infrared or nuclear magnetic resonance spectral (NMR) analyses as necessary.

Embodiment 1—3-Chloro-2-(ethylthio)-2-methylpropanenitrile

In 150 ml of dichloromethane were placed 30.5 g of diethyl disulfide. After cooling to $-50°$ to $-60°$ C., 20.0 ml of sulfuryl chloride was added dropwise and then the reaction mixture was stirred at $-30°$ C. for two hours. Then 32.5 g of methacrylonitrile was added dropwise and the reaction mixture was allowed to warm to room temperature. The solvent was removed and the residue was distilled to give 65 g of product, b.p. 71.5°–72.5° C. (0.8 mm).

Embodiment 2—3-Chloro-2-(1-chloroethylthio)-2-methylpropanenitrile

In 50 ml of methylene chloride were placed 16.3 g of 3-chloro-2-(ethylthio)-2-methylpropanenitrile. This solution was cooled to 5° C. and 13.5 g of sulfuryl chloride was added dropwise. The reaction mixture was allowed to warm to room temperature. The solvent was removed and the residue was distilled at 67° C. (0.07 mm) to give 13.5 g of product.

Embodiment 3—S-(1-(1-Cyano-1-(chloromethyl)ethylthio)ethyl)O,O-Diethyl Phosphorodithioate In 25 ml of methylene chloride were placed 3.72 g of O,O-diethyl phosphorodithioic acid and 1.05 g of powdered sodium carbonate. The mixture was stirred for 1 hour and then 1.98 g of 3-chloro-2-(1-chloroethylthio)-2-methylpropanenitrile was added. The reaction mixture was stirred for 8 hours at room temperature and filtered. The filtrate was dried (NaSO4) and the solvent was removed to give 3.5 g of crude material, and volatiles were removed by heating at 130° C. at 0.05 mm to give 2.5 g of product.

Embodiment 4—O,O-Diethyl S-(1-(1-Cyano-1-(chloromethyl)ethylthio)propyl) Phosphorodithioate Following procedures similar to those described in Embodiments 1 through 3 above, the product is prepared by treating methacrylonitrile with n-propylsulfenyl chloride followed by alpha-chlorination of the resulting product and then reaction with O,O-diethyl sodium phosphorodithioate.

Embodiment 5—O,O-Diethyl S-(1-(1-cyano-1-(bromomethyl)ethylthio)ethyl) Phosphorodithioate Following procedures similar to those described in Embodiments 1 through 3 above, the desired product is prepared by treating methacrylonitrile with ethylsulfenyl bromide, followed by alpha-chlorination of the resulting product and then reaction with O,O-diethyl sodium phosphorodithioate.

Embodiment 6—Soil Activity

The test chemical is dissolved in a solvent and thoroughly incorporated into dry soil. After venting traces of solvent, the soil moisture level is brought to 9% by adding water and thoroughly mixed. Sixty grams of the moist soil is added to a 4 oz wide-mouthed jar to ½ full. Two sweet corn seeds, which have been surface sterilized in 0.2% sodium hypochlorite solution for 15 minutes and rinsed with water, are pressed into the soil near the perimeter of the jar. A small cavity of about 2.5 cc is opened in the surface of the soil and 20 *Diabrotica undecimpunctata undecimpunctata* Mannerheim (western spotted cucumber beetle) eggs are placed in the well. They are immediately covered over with fine-seived Zonolite or Vermiculite and the covering material is wetted with about 1.5 cc of water. The jar is then capped with a lid into which two 2 mm holes have been drilled for ventilation. The jars are held under lamps at 27° C. The eggs are generally two to four days old.

After one week, the jar contents are examined for the presence of live larvae, their number is recorded and the corn roots are examined for feeding damage. Compounds showing control at 3 ppm or lower rate in the first week are evaluated at subsequent weeks. Activity at 3 ppm indicates useful soil insecticidal activity.

Results of these tests were evaluated and reported as follows:

| Rating | Complete Potential | Larval Count |
|---|---|---|
| 0 | Complete control | 0 |
| 1 | Excellent | >0 to ≦3 |
| 2 | Good | >3 to ≦6 |
| 3 | Fair | >6 to ≦10 |
| 4 | Poor | >10 |

Specific results of tests with compounds of the present invention are shown in Table I below.

TABLE I

CONTROL OF *DIABROTICA UNDECEMPUNCTATA UNDECEMPUNCTATA* LARVAE IN SOIL

| Embodiment | dosage Rate (ppm) | Weeks after Treatment | | | |
|---|---|---|---|---|---|
| | | 0 | 2 | 4 | 8 |
| 3 | 3.0 | 0 | 0 | 0 | 0 |
| | 1.0 | 0 | 0 | 0 | 0 |
| | 0.3 | 2 | 3 | 3 | 3 |

What is claimed is:

1. A compound of the formula I

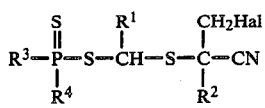

wherein $R^1$ and $R^2$ each independently is a methyl group or an ethyl group; $R^3$ and $R^4$ each independently is an alkoxy group containing from 1 to 4 carbon atoms and Hal is a chlorine or bromine atom.

2. A compound according to claim 1 wherein $R^3$ and $R^4$ each independently is an alkoxy group containing 1 to 2 carbon atoms.

3. A compound according to claim 2 wherein $R^3$ and $R^4$ each is an ethyl group.

4. A compound according to claim 3 wherein $R^1$ and $R^2$ each is a methyl group.

5. A compound according to claim 4 wherein Hal is a chlorine group.

6. A pesticidal composition comprises a pesticidally effective amount of a compound according to claim 1 and at least one carrier or surface-active agent.

7. A method for combating pests at a locus, which comprises applying to the locus or the pests, a pesticidally-effective amount of a compound according to claim 1.

8. A method according to claim 7 wherein the pests are insects or their larvae in the soil, which are damaging to plants.

9. A method according to claim 8 wherein the insect pests or their larvae are from the species *Diabrotica*.

* * * * *